(12) United States Patent
Lahrmann

(10) Patent No.: US 11,954,593 B2
(45) Date of Patent: Apr. 9, 2024

(54) METHOD TO DETERMINE A DEGREE OF ABNORMALITY, A RESPECTIVE COMPUTER READABLE MEDIUM AND A DISTRIBUTED CANCER ANALYSIS SYSTEM

(71) Applicant: H-Labs GmbH, Heidelberg (DE)

(72) Inventor: Bernd Lahrmann, Diepholz (DE)

(73) Assignee: H-Labs GmbH, Heidelberg (DE)

( * ) Notice: Subject to any disclaimer, the term of this patent is extended or adjusted under 35 U.S.C. 154(b) by 574 days.

(21) Appl. No.: 17/254,970

(22) PCT Filed: Jun. 19, 2019

(86) PCT No.: PCT/EP2019/066158
§ 371 (c)(1),
(2) Date: Dec. 22, 2020

(87) PCT Pub. No.: WO2019/243405
PCT Pub. Date: Dec. 26, 2019

(65) Prior Publication Data
US 2021/0142908 A1    May 13, 2021

(30) Foreign Application Priority Data
Jun. 22, 2018  (IE) .................................... 2018/0171

(51) Int. Cl.
*G06N 3/08*  (2023.01)
*G06F 18/21*  (2023.01)
(Continued)

(52) U.S. Cl.
CPC ........... *G06N 3/08* (2013.01); *G06F 18/2178* (2023.01); *G06F 18/2193* (2023.01);
(Continued)

(58) Field of Classification Search
CPC ........ G06N 3/08; G16H 10/40; G06V 10/454; H04L 9/50; H04L 9/3236; H04L 9/3239;
(Continued)

(56) References Cited

U.S. PATENT DOCUMENTS

2015/0213302 A1   7/2015 Madabhushi et al.
2017/0053398 A1   2/2017 Mahoor et al.
(Continued)

FOREIGN PATENT DOCUMENTS

CN        107368670 A    11/2017
CN        107368671 A    11/2017
(Continued)

OTHER PUBLICATIONS

Holzinger et al., "Towards the Augmented Pathologist: Challenges of Explainable-AI in Digital Pathology," https://doi.org/10.48550/arXiv.1712.06657, Dec. 18, 2017. (Year: 2017).*
(Continued)

*Primary Examiner* — Ross Varndell

(57) ABSTRACT

Current cancer screening methods are not suitable to be applied on a broad scale and are not transparent to the patient. The problem is solved by a method to determine a degree of abnormality, the method comprising the following steps: receiving a whole slide image, the whole slide image depicting at least a portion of a cell, classifying at least one image tile of the whole slide image using a neural network to determine a local abnormality degree value associated with the at least one image tile, the local abnormality degree value indicating a likelihood that the associated at least one segment depicts at least a part of a cancerous cell, and determining a degree of abnormality for the whole slide image based on the local abnormality degree value for the at least one image tile.

14 Claims, 6 Drawing Sheets

(51) Int. Cl.

| | |
|---|---|
| *G06F 18/241* | (2023.01) |
| *G06N 3/04* | (2023.01) |
| *G06T 7/00* | (2017.01) |
| *G06V 10/44* | (2022.01) |
| *G06V 10/764* | (2022.01) |
| *G06V 10/82* | (2022.01) |
| *G06V 20/69* | (2022.01) |
| *G16H 10/40* | (2018.01) |
| *G16H 30/20* | (2018.01) |
| *G16H 30/40* | (2018.01) |
| *G16H 50/20* | (2018.01) |

(52) U.S. Cl.
CPC ............. *G06F 18/241* (2023.01); *G06N 3/04* (2013.01); *G06T 7/0012* (2013.01); *G06V 10/454* (2022.01); *G06V 10/764* (2022.01); *G06V 10/82* (2022.01); *G06V 20/698* (2022.01); *G16H 10/40* (2018.01); *G16H 30/20* (2018.01); *G16H 30/40* (2018.01); *G16H 50/20* (2018.01); *G06T 2207/10056* (2013.01); *G06T 2207/20081* (2013.01); *G06T 2207/20084* (2013.01); *G06T 2207/30024* (2013.01); *G06T 2207/30096* (2013.01); *G06V 2201/03* (2022.01)

(58) Field of Classification Search
CPC . G06T 2207/20021; G06T 2207/20081; G06T 2207/30096
See application file for complete search history.

(56) References Cited

U.S. PATENT DOCUMENTS

| | | | |
|---|---|---|---|
| 2017/0161891 A1 | 6/2017 | Madabhushi et al. | |
| 2018/0129911 A1* | 5/2018 | Madabhushi | ........ G06V 10/774 |
| 2020/0117690 A1* | 4/2020 | Tran | ................ G06F 16/90332 |
| 2021/0407076 A1* | 12/2021 | Wirch | .................... G06F 18/217 |
| 2023/0082710 A1* | 3/2023 | Fuchs | ................ G06V 10/7635 |

FOREIGN PATENT DOCUMENTS

| | | |
|---|---|---|
| CN | 107369151 A | 11/2017 |
| WO | 2013049153 A2 | 4/2013 |
| WO | 2015189264 A1 | 12/2015 |

OTHER PUBLICATIONS

Cagatay Bilgin et al. Cell-Graph Mining for Breast Tissue Modeling and Classification; Engineering in Medicine and Biology Society (EMBC), Aug. 1, 2007; pp. 5311-5314.
Intellectual Property Office of Ireland; Office Action for related application S2018/0171; Dr. Karen Ryan; dated Mar. 23, 2020; 2 pages.
Patent Cooperation Treaty: International Search Report and Written Opinion for PCT/EP2019/066158; Carmen Rabasa Garcia; dated Nov. 14, 2019; 21 pages.
National Intellectual Property Administration, PRC: Notification of the First Examination Report of CN 201980049827.2 (related application); dated Nov. 23, 2023; Panpan WAN; 33 pages.
U.S. Appl. No. 62/647,002, filed Mar. 23, 2018; 36 Pages.
U.S. Appl. No. 62/670,432, filed May 11, 2018, 50 Pages.

* cited by examiner

METHOD TO DETERMINE A DEGREE OF ABNORMALITY, A RESPECTIVE COMPUTER READABLE MEDIUM AND A DISTRIBUTED CANCER ANALYSIS SYSTEM

CROSS-REFERENCE TO RELATED APPLICATIONS

This application is a U.S. National Phase application submitted under 35 U.S.C. § 371 of Patent Cooperation Treaty application serial no. PCT/EP2019/066158, filed Jun. 19, 2019, and entitled A METHOD TO DETERMINE A DEGREE OF ABNORMALITY, A RESPECTIVE COMPUTER READABLE MEDIUM AND A DISTRIBUTED CANCER ANALYSIS SYSTEM, which application claims priority to Irish patent application serial no. S2018/0171, filed Jun. 22, 2018, and entitled A METHOD TO DETERMINE A DEGREE OF ABNORMALITY, A RESPECTIVE COMPUTER READABLE MEDIUM AND A DISTRIBUTED CANCER ANALYSIS SYSTEM.

Patent Cooperation Treaty application serial no. PCT/EP2019/066158, published as WO 2019/243405 A1, and Irish patent application serial no. S2018/0171, are incorporated herein by reference.

TECHNICAL FIELD

The present application is directed towards a method to determine a degree of abnormality, a respective computer readable medium and a distributed cancer analysis system.

BACKGROUND

Cancer screening programs rely on consistent and early detection of cancer lesions through a trusted expert. If cancer is detected early enough, it can be treated locally and thus the health risk for the patient can usually be efficiently and effectively avoided. In many cases, cancer screening involves taking biopsies, the biopsies being small tissue samples of potentially cancerous regions. Such biopsies are usually taken during a routine medical checkup or upon special indications following preceding medical tests. Biopsies, as any other pathological tissue specimen, are evaluated after their preparation on a glass slide through an expert, usually a Board certified pathologist. The pathologist has been trained inside the community of available experts to a certain degree and is solely responsible for the diagnostics. Often, pathologists request a second opinion from colleagues. The patient himself is usually not aware and does not know anything about the diagnostic process of the tissue specimen, never meets and doesn't know anything about the person or his qualification making this important medical decision for him or her. As a result, the patient is the end dependent on a rather non-transparent process. This process results in a limited trust of the relevant stakeholders in the overall system. This feeling can be objectively supported through many studies, which have shown considerable variations of the quality of medical decisions in cancer diagnostics. Moreover, there is no gold standard in the evaluation of pathological samples, leading to a big variation in the diagnostic results. Thus, there is a need for an objective screening method that yields comparable results and which is transparent for the participating parties.

SUMMARY

Cervical cancer is one of the leading causes of cancer death among women. Worldwide. Cervical cancer is the fourth most frequently occurring malignancy in women and results in an estimated 530,000 new cases annually with 270,000 deaths. In addition, approximately 85% of the worldwide deaths from cervical cancer occur in underdeveloped or developing countries, and the death rate is 18 times higher in low income and middle-income countries compared with wealthy countries.

Recognition that cervical neoplasia begins as an intraepithelial change, which usually takes many years to develop into an invasive disease, led to the use of cervical exfoliative cytology (e.g. with the brush) in screening. In this way, detected cervical intraepithelial neoplasia may be treated early to prevent the development of cervical cancer. Cervical cancer screening is recommended for all sexually active women worldwide.

Currently, such screening is based mainly on the morphological and cytological examination of cytosmears of the cervix uteri, what is called the PAP test, which is made on the basis of gynecological routine examinations at regular intervals for sexually active women. Unfortunately, up to 30-50% of the results of the PAP test are false negative, rendering PAP testing not a satisfying solution. Moreover, PAP testing has not been efficiently implemented in many low income and middle income countries. Thus, over 85% of global cancer cases and related deaths occur in these countries.

Genetic testing through, for example, sequencing technology is a further diagnostic possibility, which is upcoming for nearly all cancer types. Still, genetic testing has an insufficient test specificity. Genetic testing alone, however, is insufficient.

In this line, to support the genetic HPV testing in cervical cancer screening, biomarker-based immunocytology plays a critical role. For example, tests are used for cell samples using p16 and Ki67 proteins in a dual stain in connection with liquid-based cytology. These tests show promising results in primary screening and as a triage of HPV positive for women. Unfortunately, the good accuracy results of these tests have so far only been reached in an optimal setting with specifically trained human experts. As a result, the accuracy also depends heavily on the human expert.

Samples of each cancer type show a very specific collection of morphological features. Pathologists are trained often for at least a decade before they become experts in usually just a few specific fields. In each field, they are trained to recognize specific patterns indicative of specific disease forms or also different cancer grades (in cervical cancer, e.g. cervical intraepithelial neoplasia grades are quantified through numbers 0-3). This is even more complicated when histological or cytological biomarkers are used which highlight specific spatial patterns. Unfortunately, despite the fact that standard protocols for such tests are usually specified and predetermined, there is further considerable variability introduced between laboratories. For example, unavoidable interlaboratory differences in the chemical behavior of the substances used for preparing and performing the actual sample staining leads to variability.

The most important factor, which introduces variation in overall diagnostics, is the human expert itself. Humans are very good at visual interpretation of spatial patterns and are often able to reproduce decisions with high accuracy because they tend to stick to the decision patterns established in their own brains. This, however, leads to high inter-observer variation in a larger group of human experts.

In conclusion, when considering all regional differences and also takes the variability of the underlying experimental processes in the laboratories into account as well as the different experts, it is clear that the combination of all these factors in the diagnostic process will lead to a large variability in the diagnostic quality.

Even more, biomarker-based immunocytology-based tests, such as the Roche-Ventana CINtec test are provided with an extensive documentation. Even in its very general workflow, it requires the expert to follow very complex visual screening procedures. Moreover, very complex decisions need to be made, which are hardly possible to follow in an objective fashion, even for an expert. There are specific criteria given for dual stained cervical epithelial cells comprising the spatial location of p16 and Ki67 like for example their co-localization within the same cell in a specific appearance, so that for example a red nucleus must be within the same microscopy plane as a brown stain. The expert then has to decide if the staining intensity is "weak" or "strong" to correctly apply the test. This is very difficult. Furthermore, Ki67 signal intensity (red) may be uniformly stained with the nucleus containing a speckled or granular staining pattern and red staining of nucleoli while negative cells comprise cervical epithelial cells stain with only one blue counterstain, or only brown and/or nuclear stain or only with a red nuclear stain. This very general set of criteria is then specified with examples of all different kinds of patterns of these types on over 70 pages. A general specific procedure is described for the overall slide requesting a cytologist or pathologist to systematically scan the full slide at 10× or 20× times magnification for cancer events in a snakelike fashion. One specific problem also addressed in the above-mentioned documentation is the handling of cell clusters, which may appear and have dedicated further special protocols describing their evaluation.

All those examples show that the interpretation of cytological tests like the CINtec plus test is very complicated, very hard to standardize and reproduce. Accordingly, it is clear that inter-observer variation is the most critical challenge for such tests.

In conclusion, the analysis of cytological or histological biopsies in cancer screening is based on the visual interpretation of images as described above. Visual interpretation can be accomplished using artificial neural networks, for example. In recent years, deep learning-based artificial neural networks have gained attraction in many fields and accomplished very good accuracy in recognizing patterns. In general, artificial neural networks and artificial intelligence in general have been used in clinical decision support systems since the early days of computing. Except for cytology evaluation, artificial neural networks have been used for lung cancer screening in radiology images. Starting in the 1990's, the concept of neural networks in cytopathology was suggested. Generally, artificial neural networks when properly trained have the ability to tolerate ambiguous and noisy data. Artificial neural networks were proposed to be used alongside other traditional algorithmic processing technics for the development of systems useful in quantitative pathology. The vast majority of neural network applications are for cervical pathology, which this invention further extends.

The majority of the proposed neural network applications are related to breast and thyroid cytopathology as well as cytopathology of the urinary tract. Neural networks have been applied to a smaller degree in cytopathology of the gastrointestinal system and to a lesser degree in effusion cytopathology. Still, there are cytopathology sub disciplines that have not yet used neural networks, especially cytopathology of the lymph node, respiratory system, soft tissues, bone and skin, liver and pancreas, central nervous system and the eye, among others. Additionally, the presently available algorithms use no contextual information and nearly exclusively refrain from cell nuclear features. Usually, noise which is disturbing the diagnosis (for example cooloid presence in the thyroid cytopathology) is not considered. The available algorithms heavily depend on both staining and cell characteristics of each tissue type and anatomical site.

Finally, adding new knowledge to neural networks is a great problem, as robustness and classification may be undermined by overfitting of the training data.

It is therefore an object of the present invention to provide a method and a system to detect cancerous cells to a sufficient degree of certainty. Moreover, it is an object of the present invention to provide a method and system that is able to process whole slide images in an automatic way. Additionally, it is an object of the present invention to reduce the variability of test results. Even more, it is an object of the present invention to reduce the costs and processing time of cell testing. In addition, it is an object of the present invention to make the process of diagnostics transparent to the patient.

The objects of the present invention are solved by the subject matter of claims 1, 12 and 13.

In particular, the object of the present invention is solved by a method to determine a degree of abnormality, the method comprising the following steps:
  a) receiving a whole slide image, the whole slide image depicting at least a portion of a cell, in particular a human cell;
  b) classifying at least one image tile of the whole slide image using a neural network to determine a local abnormality degree value associated with at least one image tile, the local abnormality degree value indicating a likelihood that the associated at least one portion depicts at least a part of a cancerous cell; and
  c) determining a degree of abnormality for the whole slide image based on the local abnormality degree value for the at least one image tile.

A core aspect of the present invention is the fact that a whole slide image may be automatically processed using a neural network to determine a degree of abnormality. Thus, no separate feature detectors, for example corner detectors, are necessary. Thus, the present invention provides end-to-end learning system, relying on neural network technology. Moreover, each layer in a neural network resembles hard criteria that are used to evaluate the image tile, i.e. each layer functions as an elaborate feature detector. Thus, using a neural network has the further advantage that comparable results are achieved. Additionally, a further advantage lies in the segmentation of the whole slide image into at least one image tile. Thus, each image tile may be processed in parallel, resulting in better processing speeds. The present invention also allows for processing each step of the above-mentioned method at different locations. For example, the whole slide image may be generated at a first location, and the classifying and determining may be conducted at a second location. Thus, a global application of the described method is easily achieved. As a result, the cost-per-test drops significantly. In the context of this application, the term "local" may be interpreted as relating to a specific area on the whole slide image, to particular characteristics of the whole slide image, e.g. color channels or further characteristics of the whole slide image.

In one embodiment, the method may comprise segmenting the whole slide image into a plurality of image tiles, the size of each image tile being equal, in particular using a K means clustering algorithm.

The method can thus also include a segmenting step, wherein the whole slide image is segmented into a plurality of image tiles. Preferably, the size of the image tiles is equal, for example a square. In one embodiment, the size of the image tiles is dependent on the implementation of the neural network. For example, the neural network can be implemented as a convolutional neural network, wherein the size of a tile is dependent on a kernel definition. Consequently, very efficient implementations of a neural network are possible.

In one embodiment, the degree of abnormality for the whole slide image may be indicated by a function, in particular a max-function, a statistical aggregation of the local abnormality degree value (15, a_j, 519, 719, 719', 719") or an average function dependent on the local abnormality degree value (15, a_j, 519, 719, 719', 719").

Using a function to determine the degree of abnormality has the advantage that the appropriate method may be used to determine the degree of abnormality. Thus, in some cases using a max-function that is adapted to determine the maximum value of the local abnormality degree values may yield good results. In other cases it may be more appropriate to compute the average of the local abnormality degree values. In one embodiment, the function is dependent on the disease and/or type of cancer to be detected.

In one embodiment, the size of each image tile may be within an interval of 32×32 pixel to 1000×1000 pixel, 200×200 pixel to 700×700 pixel or larger than 1000×1000 pixel.

In one embodiment, the neural network is implemented as a convolutional neural network, the neural network comprising:
- at least fifty layers,
- at least twenty pooling layers,
- at least forty convolutional layers,
- at least twenty kernels in at least one the convolutional layer,
- at least one fully connected layer,
- a softmax-classifier layer and/or
- neurons using logit and/or logistic functions as activating functions.

In one embodiment, the last layer of the neural network may be made of a softmax-classifier layer with two classes.

As a consequence of the above described embodiment, a big variability of neural network implementations are possible. Importantly, using a deeper network, i.e. more layers, often increases accuracy of the classification results when combined with respective pooling, subsampling and kernel definitions. For example, networks having more than fifty layers, preferably more than eighty layers, are able to detect and generalize more elaborate sub structures of an image tile. In one preferred embodiment, a soft-max classifier layer is used as a last layer, indicating the final result of the classification process. Thus, a discrete set of classes, preferably two, can be used as classification result data.

In one embodiment, the method may comprise training the neural network with training data stored in a knowledge base, the training data including a plurality of tuples, each tuple indicating an image tile, a training abnormality value and a likelihood value.

To train a neural network, usually a large number of training samples are needed. For the present invention, these samples include data concerning the image tile, a training abnormality value and/or a likelihood value. The training abnormality value may comprise a degree of cancer, for example a Gleason value or Gleason score, which is a value between 1 and 5. In the case of a Gleason value, a score of 1 indicates that a cancerous prostate closely resembles normal prostate tissue. A score of 5 indicates that the tissue does not have any or only a few recognizable glands. The values between 1 and 5 are gradations of the grades 1 and 5. The likelihood value indicates a confidence in the training abnormality value. Thus, a very high likelihood value indicates that the assignment of the training abnormality value to the respective image tile is most likely true. The image tile may be stored as a pointer or a link in the tuple, so that not the entire image tile needs to be stored in the knowledge base. This reduces the necessary data to store in the knowledge base itself and improves look-up speed in case the tile itself is not needed. The training abnormality value may be represented as a floating point or an integer value. The likelihood value may be stored as a floating point.

In one embodiment, the method may comprise:
Receiving an update whole slide image to update the knowledgebase;
Segmenting the update whole slide image into a plurality of image tiles;
Determining a training abnormality degree value for each image tile of at least one subset of the plurality of image tiles, in particular by a human expert;
Updating the knowledgebase with the subset of the plurality of image tiles and the associated training abnormality degree values if it is determined that adding the subset of the plurality of image tiles and the associated training abnormality degree values improves the accuracy of the neural network when trained with the updated knowledgebase.

The aforementioned embodiment allows the efficient updating of the knowledge base to train the neural network. That is, the knowledge base is only updated if it is determined that the update actually improves the accuracy of the prediction conducted by the neural network. This embodiment thus prevents unnecessary knowledge base updates, which do not actually enhance the capabilities of the process.

In one embodiment, the updating of the knowledge base may further comprise:
Computing a predicted abnormality degree value and an associated likelihood value for each of the plurality of image tiles using the neural network;
Determining a priority value based on the predicted abnormality degree value and the associated likelihood value for each of the plurality of image tiles; and
Determining the subset of the image tiles based on the determined priority values.

In one embodiment, the priority value is computed by using a 2-dimensional priority mapping function p(d,1)→ [0,1], calculated as $$p(a, l) := \frac{a*0.8 + l*0.2}{5}$$

"a" being the abnormality value and "l" being the likelihood value. Using this priority value, the subset of image tiles may be determined using a threshold value, wherein only image tiles are added to the subset that have a priority value greater than the threshold value. As a result, the above-mentioned embodiment provides a preselection of image tiles to be considered by the expert. Thus, the number of image tiles to be reviewed and to be sent to the is reduced. Consequently, the amount of data to be sent to the experts is reduced.

In one embodiment, determining that adding the subset of the image tiles and the associated training abnormality degree values improves the accuracy of the neural network when trained with the updated knowledge base may comprise:

Updating a validation database with the subset of the image tiles and the associated training abnormality degree values, the validation database in particular including at least a subset of the knowledge base;

Training the neural network using the validation database;

Using the neural network trained on the validation database to predict the data in an independent validation cohort to compute a first accuracy value;

Using the neural network trained on the knowledgebase to predict the data in the independent validation cohort to compute a second accuracy value;

Comparing the first and the second accuracy values to determine whether adding the subset of the image tiles and the associated abnormality degree values improves the accuracy of the neural network when trained with the updated knowledgebase.

Thus, a total of three databases may be used for the inventive method. The knowledge base may capture the knowledge that presently produces a neural network that results in the best accuracy. The validation database may capture the data of the knowledge base plus additional data of experts that may lead to better accuracy results for the prediction using the neural network. The independent validation cohort stores ground truth data, which may be used to test the accuracy of a neural network trained on the knowledge base and a neural network trained on the validation base. By this, two neural network implementations may be compared and the best may be selected for further processing.

In one embodiment, the method may comprise storing the training abnormality degree value for each of at least a subset of the image tiles determined by a human expert in a block of a blockchain.

Storing the knowledge of a human expert in a blockchain allows using a distributed data structure that records transactions. Importantly, when storing the training abnormality degree value and an indication of the image tiles in the blockchain, it is highly transparent to the patient and other doctors/experts, which data was used to train the neural network that was used to classify his or her tissue sample. As a result, the inventive method provides a transparent solution, wherein the patient, other experts and doctors always knows what knowledge contributed to the assessment of the patient's tissue samples.

In one embodiment, the blockchain indicates the image tiles, in particular using a link and/or a pointer, the associated training abnormality degree values and the expert determining the abnormality degree value of the training data stored in the knowledge base.

In one embodiment, each block of the blockchain comprises a header, comprising a hash value of the header of a previous block and a hash value of the root node of a Merkle tree, the Merkle tree indicating all data stored in the knowledge base.

The blockchain therefore is a chain of blocks, wherein the blocks are linked to each other via pointer which may be hash values. Adding a new assessment of an expert, i.e. a new training abnormality degree value and the associated image tile, to the knowledge base represents a transaction, which is recorded by the blockchain. For this, each block stores a link to an associated image tile as well as the associated whole slide image and in particular the expert that made the assessment of a training abnormality degree value. Since a blockchain usually is a public ledger of transaction, using a link to indicate the associated image tiles has the benefit that unauthorized users cannot access the image data used to train a neural network but merely can access the assessments associated with the images. Thus, the image tiles are protected from unauthorized access.

In one embodiment, a reward function may be associated with each human expert contributing assessments to the blockchain, in particular using an identification number, the value of the reward function in particular being dependent on the number of contributions made by the associated human expert.

Using a reward function has the benefit that experts can be motivated to contribute data that may be used for training the neural network and thus improve the accuracy of the neural network. The reward function could, for example, trigger the payment of an amount of money in some currency, for example bitcoin or any other currency, to the human expert as a reward for the contribution. Moreover, the value to be paid to the expert could vary depending on the number of contributions already added by the particular human expert. For example, the reward function could be modelled using a falling exponential function. Thus, a high value, for example 10, could be the initial reward for the $1^{st}$ contribution, and a low value, for example 1, could be the reward for the $10^{th}$ contribution. This makes first-time contributions more attractive for an expert and prevents flooding of the blockchain with bogus and low-quality data.

In one embodiment, the blockchain may implement the validation database.

In one embodiment, the value of the reward function may further be dependent on the number of contributions of the associated human expert that improve the accuracy value of a neural network trained at least partially on the assessments of the associated human expert and determined by predicting the independent validation cohort.

It is of further advantage if the reward function is not only dependent on the number of contributions but also on the quality of each contribution. Thus, in case the contribution improves the prediction accuracy of a neural network trained with the contribution over the prediction accuracy of a neural network without the contribution, a higher reward is warranted. This ensures that human experts are motivated to contribute a high number of high quality assessments. Moreover, flooding of the blockchain with low quality assessments is prevented.

In one embodiment, the reward function may be implemented as a smart contract on the blockchain.

In one embodiment, the blockchain may implement a scripting language, wherein the smart contract may be implemented as a script in the scripting language associated with a transaction on the blockchain, wherein the script may be executed when a new block that comprises the script, is added to the blockchain.

Consequently, a smart contract can be used to implement the reward function. This provides a fully automatic mechanism to add new data to the blockchain and reward the human experts providing the new data. Thus, a very efficient implementation of such a scheme is provided.

In conclusion, using a blockchain to store the assessments of the human expert gives rise to elaborate feedback loops to improve the accuracy of the neural network.

In one embodiment, each block of the blockchain may further comprise meta-data, the meta-data comprising an indication of the geographic location of the human expert, the qualification of the human expert, the years of experience of the human expert and/or an association the human expert is part of.

In one embodiment, the method may further comprise selecting at least a subset of the data stored in the blockchain as the validation database.

In one embodiment, the subset of the data stored in the blockchain may be selected based on the meta-data stored in the blockchain.

With the above-mentioned embodiments, it is possible to filter the data used for training the neural network based on the meta-data. For example, it may be necessary due to regulatory restrictions, to train the neural network only on data contributed by experts that practice in a specific country. The above-mentioned embodiments provide an easy way to accommodate for such requirements.

In one embodiment, the method further comprises storing an indication of the neural network, e.g. a hash value of the neural network, in a second blockchain. The indication may comprise a further indication to all training data used to train the neural network.

In the scope of this patent application, blockchain may refer to any digital ledger technology, such as blockchain, tangle or hashgraph.

With the above-described embodiment, an immutable version history of the neural networks is provided. Thus, it is highly transparent to each stakeholder which data is used in what version of the neural network.

In particular the problem is also solved by a computer readable medium storing instructions that when executed by at least one processor cause the at least one processor to implement a method according to any of the aforementioned embodiments.

The advantages of the above-mentioned solution are similar or equal to the method.

In particular, the problem is also solved by a distributed cancer analysis system, comprising the following components:
  a segmentation entity adapted to receive a whole slide image, the whole slide image depicting at least a portion of a cell, in particular a human cell;
  a computation entity adapted to compute a degree of abnormality for the whole slide image using a neural network.

In one embodiment, the distributed cancer analysis system may comprise a knowledgebase comprising training data, wherein the computation entity is further adapted to train the neural network using the training data.

In one embodiment, the computation entity may be adapted to compute the degree of abnormality for the whole slide image using a function, in particular a max-function, a statistical aggregation of local abnormality degree values associated with the at least one images tile and/or an average function dependent on local abnormality degree values associated with the at least one image tile.

In one embodiment, the distributed cancer analysis system may comprise a communication interface adapted to distribute at least one subset of a plurality of image tiles to at least one expert, wherein the segmentation entity is further adapted to segment the whole slide image into the plurality of images tiles.

In one embodiment, the distributed cancer analysis system may comprise a priorization entity adapted to determine a subset of the image tiles to be transmitted to the at least one expert by the communication interface, wherein the priorization entity may further be adapted to determine the subset of candidate image tiles based on a computed priority value for each image tile.

In one embodiment, the distributed cancer analysis system may comprise a testing entity adapted to:
  receive validation training data of a validation database, the validation training data comprising at least one validation set, the validation database in particular including at least a subset of the knowledge base, determined by the at least one expert;
  training the neural network using the received validation data;
  using the neural network trained on the validation data to predict the data in an independent validation cohort to compute a first accuracy value;
  using the neural network trained on the knowledgebase to predict the data in an independent validation cohort to compute a first accuracy value;
  comparing the first and the second accuracy values to determine whether adding the subset of the image tiles and associated training abnormality degree values improves the accuracy of the neural network when trained with the updated knowledgebase.

In one embodiment, the distributed cancer analysis system further comprises a blockchain adapted to store the training abnormality degree value for each of at least a subset of the image tiles in a block, the training abnormality degree value determined by a human expert.

In one embodiment, the blockchain may be adapted to indicate the image tiles, the associated training abnormality degree values and the experts determining the training abnormality degree values of the training data stored in a knowledge base.

In one embodiment, each block of the blockchain may comprise a header, the header comprising a hash value of the header of a previous block and a hash value of a root node of a Merkle tree, the Merkle tree indicating all data stored in the knowledgebase.

The benefits and advantages of the aforementioned distributed cancer analysis system are equal or similar to the advantages of the above-mentioned method to determine a degree of abnormality.

In an alternative embodiment, the determining step of the method may determine a value indicative of an abnormality for the whole slide image based on local values, indicative of local abnormality values, for the at least one image tile.

In one embodiment, the value indicative of an abnormality may indicate the area of abnormal glands, in particular in a prostate, and/or a tissue area.

The alternative method therefor allows for the identification of the area that is affected by cancerous tissue, e.g. 50% of the whole slide image.

Further embodiments are indicated by the dependent claims.

BRIEF DESCRIPTION OF THE DRAWINGS

In the following, embodiments of the invention are described with respect to the figures, wherein.

DETAILED DESCRIPTION

Figure 1:
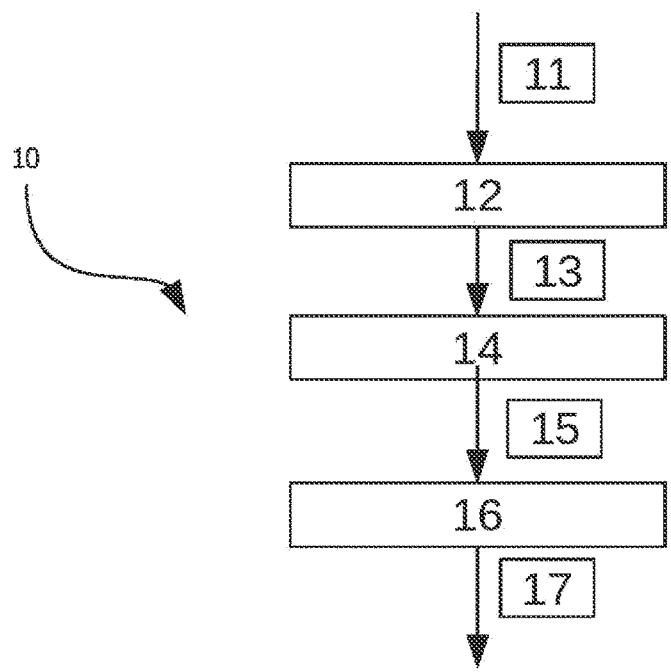
FIG. 1 shows a flow diagram of the method to determine a degree of abnormality.

FIG. 1 shows a flow diagram of a method to determine a abnormality degree value 10. In a first step, a whole slide image 11 is processed during a segmentation phase 12. The whole slide image 11 depicts a portion of a human cell that may be cancerous. Moreover, the whole slide image 11 may show a cell that has been treated with biomarkers, for example of the CINTEC test. Thus, certain regions in the whole slide image appear colored indicating certain chemical reactions. The whole slide image 11 is then segmented in the segmentation phase 12 into a plurality of image tiles 13. Each image tile represents a portion of the whole slide image. Thus, the plurality of image tiles 13 together form the whole slide image 11. Preferably, the image tiles 13 are of a same size. In the present embodiment, the image tiles 13 are each of a size of 30×30 pixels. In other embodiments, other tile sizes are possible, for example the sizes of a 100×100 pixels, 200×200 pixels or 1000×1000 pixels. The whole slide image 11 is usually of a very high resolution, for example comprising more than 16 million pixels.

In a next step, the image tiles 13 are processed in a prediction phase 14, wherein a local abnormality degree value 15 is computed for each image tile. In the present embodiment, this local abnormality degree value 15 is computed by a convolutional neural network. Importantly, each image tile 13 may be processed in parallel. The architecture of the neural network will be explained in detail with respect to FIG. 9.

Having determined a local abnormality degree value 15 for each image tile 13, a degree of abnormality 17 is computed during an evaluation phase 16. Thus, the abnormality degree value 17 is based on the plurality of image tiles 13. In the present embodiment, the degree of abnormality 17 is merely the maximum value of the different local abnormality degree values 15 for each image tile. This is due to the fact that for a human cell to be cancerous, it may be sufficient that a single part of the human cell shows a cancerous characteristic.

Figure 2:
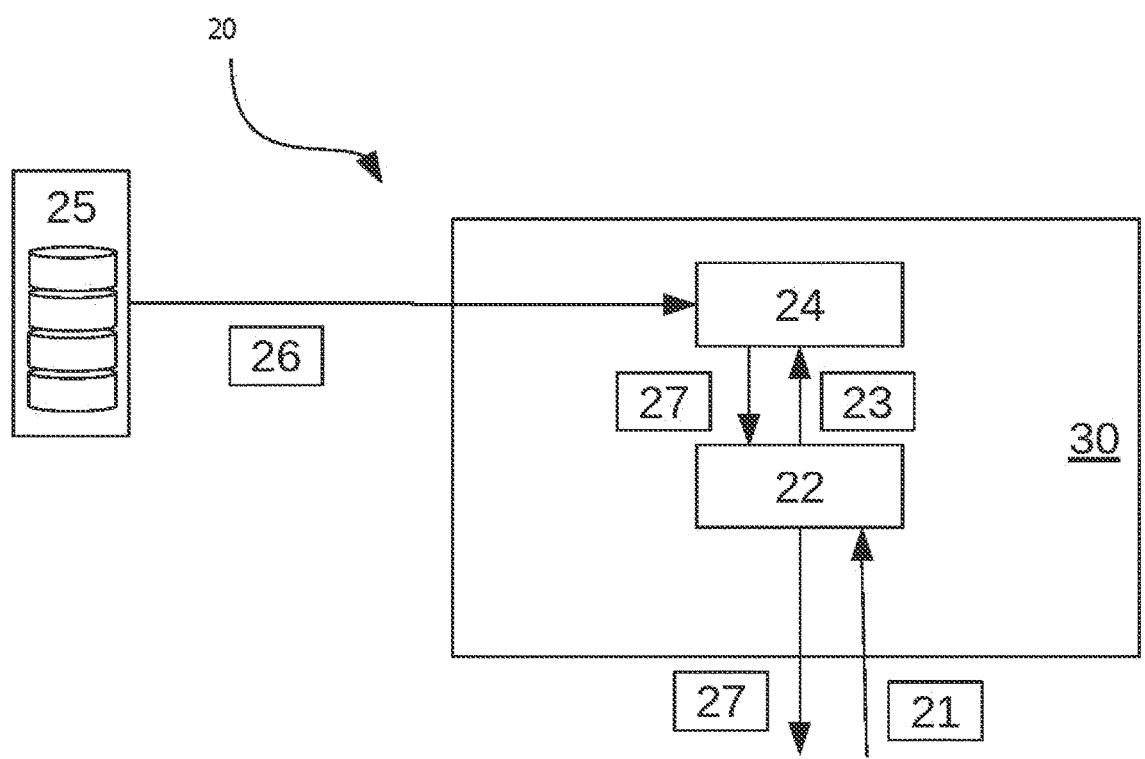
FIG. 2 shows a schematic of a system to determine a degree of abnormality.

FIG. 2 shows a respective system, implementing the method of FIG. 1. The system 20 of FIG. 2 comprises an image processing entity 30, which comprises a segmentation entity 22 as well as a computation entity 24. The computation entity 24 is communicatively coupled to a database 25, storing training data 26, which is used by the computation entity 24 to train a neural network. The neural network is adapted to determine abnormality degree values. For example, a whole slide image 21 is read by the segmentation entity 22. The segmentation entity 22 is adapted to segment the whole slide image 21 into a plurality of image tiles 23. The plurality of image tiles 23 may be stored as a set, or as an array. Other data structures are possible as well, for example a hash map or a sorted list. The computation entity 24 is further adapted to process the plurality of image tiles 23 to determine a result 27, i.e. a degree of abnormality. For this, the computation entity 24 uses a neural network to process each of the tiles of the plurality of tiles 23. The degree of abnormality 27 is in the end returned by the image processing entity 30 to the user.

In the embodiment shown in FIG. 2, the knowledge base 25 may be stored remotely from the image processing entity 30. Thus, the communication link between the knowledge base 25 and the computation entity 24 may be implemented as an internet connection. Other types of networks are possible as well, for example intranets. The whole slide image 21 may be obtained in any laboratory around the world, i.e. the whole slide image 21 may also be communicated via an internet connection to the segmentation unit 22.

Figure 3:
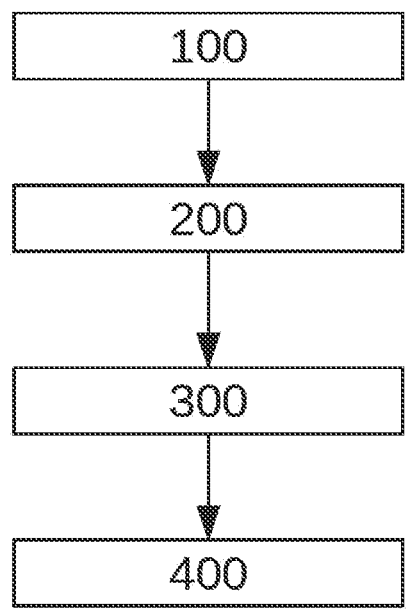
FIG. 3 illustrates a flow diagram showing the different phases of a method to improve the accuracy of the used neural network.

FIG. 3 illustrates the different phases of a method to improve the accuracy of the method shown in FIG. 1. As is evident from FIG. 3, the method comprises a prediction phase 100, a priorization phase 200, a decision making phase 300 and an improvement phase 400. The details of each phase will now be described with respect to FIGS. 4-7.

Figure 4:
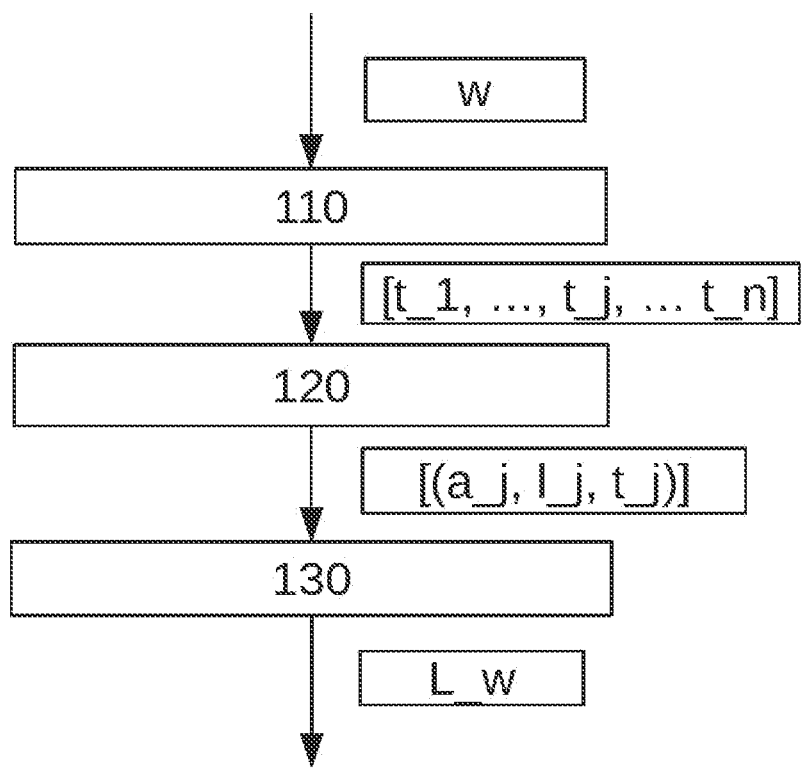
FIG. 4 illustrates a flow diagram showing the first phase of the method of FIG. 3.

FIG. 4 illustrates the different sub-phases of the prediction phase 100. In a first partitioning phase 110, the whole slide image w is segmented into a plurality of image tiles $t\_1$ to $t\_n$. In the next step, a neural network is used to predict predicted abnormality values $a\_j$ and likelihood values $l\_j$ for each image tile $t\_j$. The predicted values may be stored together with a pointer to the image tile $t\_j$ as a tuple. Consequently, an array of tuples may be generated during the abnormality prediction phase 120.

For example, the neural network may predict a tuple $(a\_1, l\_1) = (4, 30\%)$. Thus, the neural network has predicted a Gleason grade of 4 and a likelihood of 30% for the image tile $t\_1$. The same procedure is repeated for each image tile, resulting in an array with the size being equal to the number of image tiles $t\_1$ to $t\_n$ generated during the partitioning phase 110.

A complete list is generated in the list creation phase 130, wherein all predicted abnormality and likelihood values are grouped together into a list $L\_w$ along with a pointer to their respective image tiles.

Figure 5:
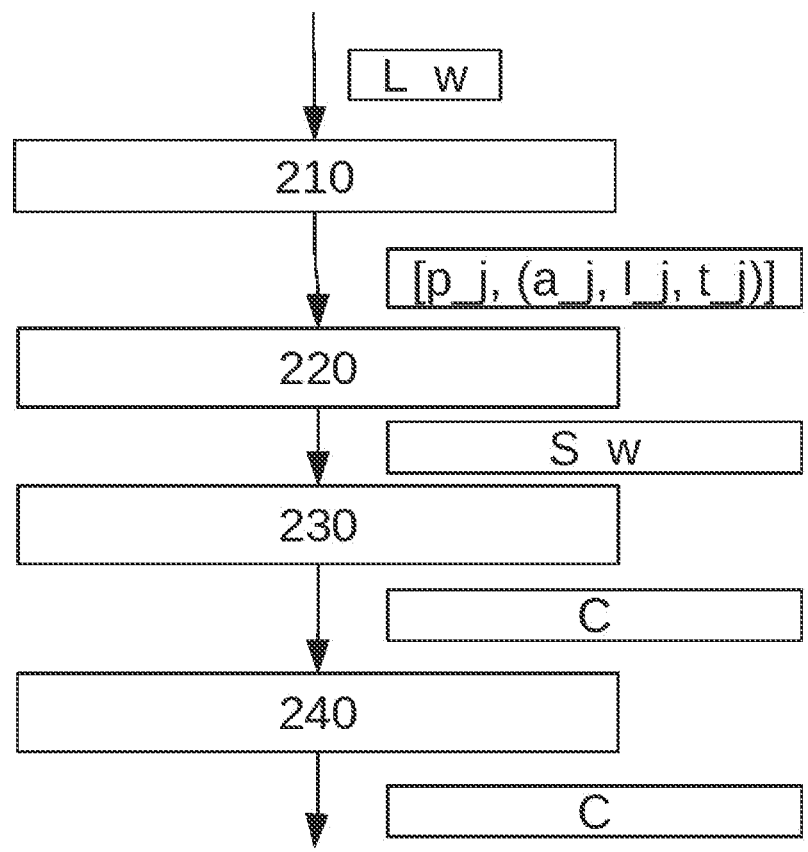
FIG. 5 illustrates a flow diagram showing the second phase of the method of FIG. 3.

FIG. 5 details the workings of the priorization phase. In a prioritizing phase the list $L\_w$ is processed. Each entry in this list, i.e. a single predicted abnormality value along with the likelihood value as well as a pointer to the associated image tile is processed using a 2-dimensional priority map function. For example, a function with the computation definition $$p(a, l) := \frac{a * 0.8 + l * 0.2}{5}$$

Thus, for the above-mentioned tuple (4, 30%) the resultant priority value is computed as follows:

$$p(a, l) := \frac{4 * 0.8 + 0,3 * 0.2}{5} = 0,65$$

The same process is repeated for each tuple stored in $L\_w$. The results are grouped together in a list of priority tuples $S\_w$, wherein each tuple has the form $(t\_j, a\_j, l\_j, p(t\_j, l\_j))$.

In a next candidate elimination phase 230, the list S_w is filtered, filtering out all tuples with a low priority. For example, all entries in the list S_w are eliminated which have a priority of lower than 0.5. The resultant list C is then distributed to experts E during a distribution phase 240. The experts E may be human experts in the field, for example pathologists. The human experts E may be located around the world and thus distribution during the distribution phase 240 may be done using an Internet or any other electronic communication means. Importantly, only the list C is distributed to the experts and not the entire list S_w.

Figure 6:
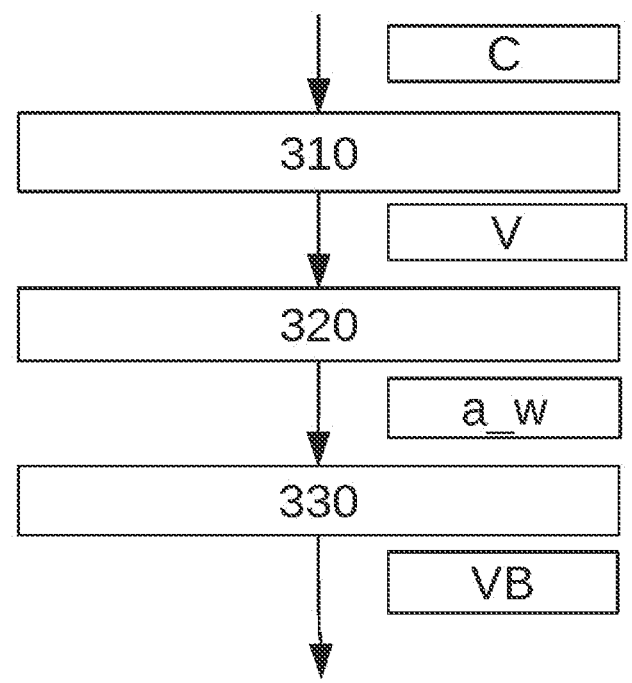
FIG. 6 illustrates a flow diagram showing the third phase of the method of FIG. 3.

FIG. 6 indicates the decision making phase 300. During a review phase 310 each expert reviews the data stored in the candidate list C. The experts use their knowledge and experience to make a decision on the respective image tiles, providing a training abnormality value and a likelihood. For example, the expert may simply agree to the predictions produced by the neural network. In another case, the expert may correct the prediction made by the neural network to a different one. The expert may be supported during this process by a graphical user interface, wherein the expert may easily review each image tile and make a decision on the training abnormality degree and likelihood value. The determination of the training abnormality is conducted by the expert during the abnormality determination phase 320. In the next phase, the different training abnormality values a_w are combined during a knowledge base extension phase 330 to generate a validation database VD. Consequently, the validation base VD comprises the data of the original knowledge base 25 used to train the neural network used to predict the predicted abnormality and likelihood values for each of the image tiles.

Figure 7:
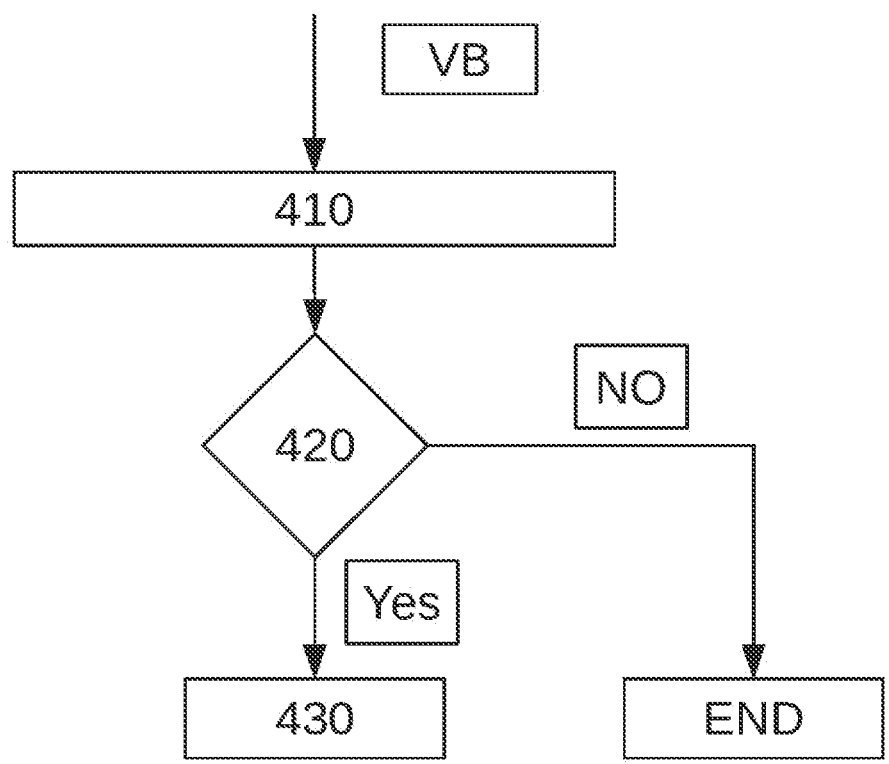
FIG. 7 illustrates a flow diagram showing the fourth phase of the method of FIG. 3.

FIG. 7 shows that the validation base VD is further processed during an accuracy comparison phase 410. During the accuracy comparison phase 410, a neural network is trained on the data stored in the validation base VD. Then, the neural network is used to predict abnormality values stored in an independent validation cohort. The independent validation cohort stores abnormality values, image tiles and likelihood values. Thus, the independent validation cohort comprises ground truth data, which can be used to compare the results of a neural network trained on the validation database VD and the original knowledge base 25.

Consequently, a first accuracy value is computed for the independent validation cohort using the neural network trained on the knowledge base 25. A second accuracy value is then computed for the neural network trained on the validation database VD. Finally, the first and the second accuracy values may be compared, indicating, which training data leads to better prediction results on the independent validation cohort. The accuracy may be computed as $$\text{Accuracy} = \frac{truePositives + trueNegatives}{truePositives + trueNegatives + falsePositives + falseNegatives}$$

Consequently, in the determination phase 420, it may be determined, which training data leads to better results. If the validation database VD leads to a better accuracy value, the method proceeds with the yes-branch, continuing with the network replacement phase 430. In the network replacement phase 430, the knowledge base 25 is replaced by the validation database VD. Also, the neural network used to compute the predictions in phase 120 is replaced by the neural network trained on the validation database VD. If the determination phase 420 finds that the knowledge base 25 leads to better results than the neural network trained on the validation database, the no-branch is used and the process ends.

Figure 8:
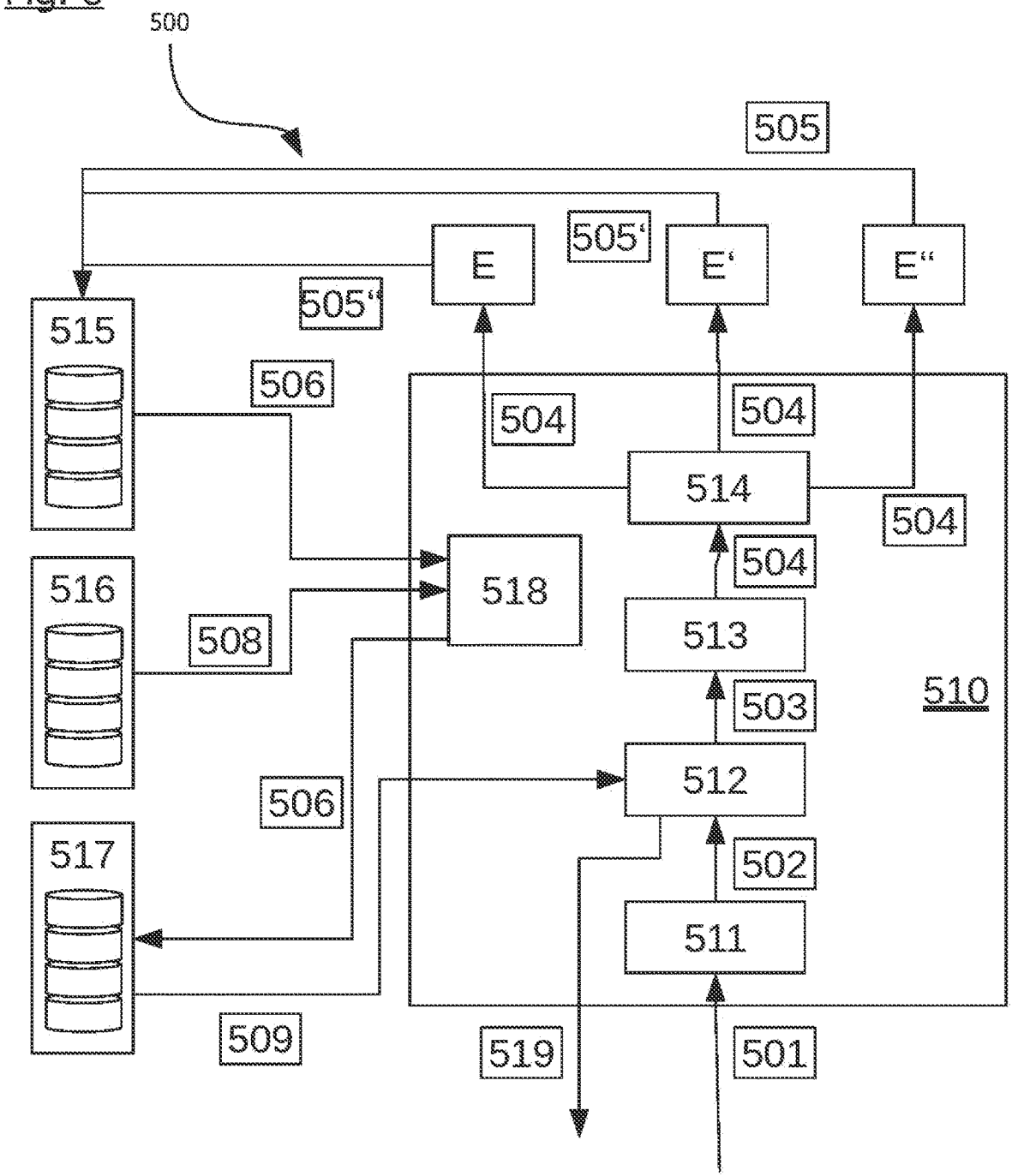
FIG. 8 illustrates a schematic of a system to improve the accuracy of the neural network.

FIG. 8 shows a system 500, which is adapted to implement the methods of FIGS. 3-7. FIG. 8 shows a distributed cancer analysis system 500 (DCAS), comprising a validation database 515, an independent validation cohort 516 and a knowledge base 517. The knowledge base 517 is communicatively coupled to a computation entity 512 of an analysis system 510. The knowledge base 517 stores training data 509, which may be used by the computation entity 512 to train a neural network to classify image tiles into local or predicted abnormality degree and likelihood pairs 503. A segmentation entity 511 is adapted to receive a whole slide image 501 and generate a set of image tiles 502, which are sent to the computation entity 512. A priorization entity 513 determines priority values, as already explained above, for the entries in the list of abnormality degree and likelihood pairs 503 as determined by the computation entity 512.

Based on the priority values, the priorization entity 513 determines a list of candidate image tiles 504 by comparing the computed priority values with a threshold value, e.g. 0.7 or 0.5. The list of candidate image tiles 504 is sent to a communication interface 514, which is communicatively connected to three experts E, E', E". The experts E, E', E" are located outside of the analysis system 510 and may be located around the world. Each expert E, E', E" processes the received list of candidate image tiles 504 to produce respective validation sets 505, 505', 505". That is, each expert E, E', E" validates the predicted abnormality degree values for the image tiles or changes the values and thus creates training abnormality degree values. Having reviewed the list of candidate image tiles 504, the experts E, E', E" send the results of the review process as validation sets 505, 505', 505" to the validation database 515. The validation database 515 comprises the training data 509 of the knowledge base 517 with the additional data obtained by the experts E, E', E".

The validation database 515 sends validation training data 506 to a testing entity 518 which is comprised in the analysis system 510. Using the validation training data 506, the testing entity 518 trains a neural network and uses the trained neural network to predict the data in an independent validation cohort 516. The independent validation cohort 516 also sends its validation data 508 to the testing entity 518. The testing entity 518 is further adapted to compute a first accuracy value for the neural network trained on the validation training data 506. The computed accuracy value is then compared to an accuracy value of the neural network trained on the training data 509 of the knowledge base 517. In case the accuracy value achieved the neural network trained on the validation training data 506 is greater than the accuracy value of the neural network trained on the training data 509 of the knowledge base, the validation training data 506 replaces the data in the knowledge base 517. Also, the neural network trained on the validation training data 506 is then used by the computation entity 512 to process image tiles.

Figure 9:
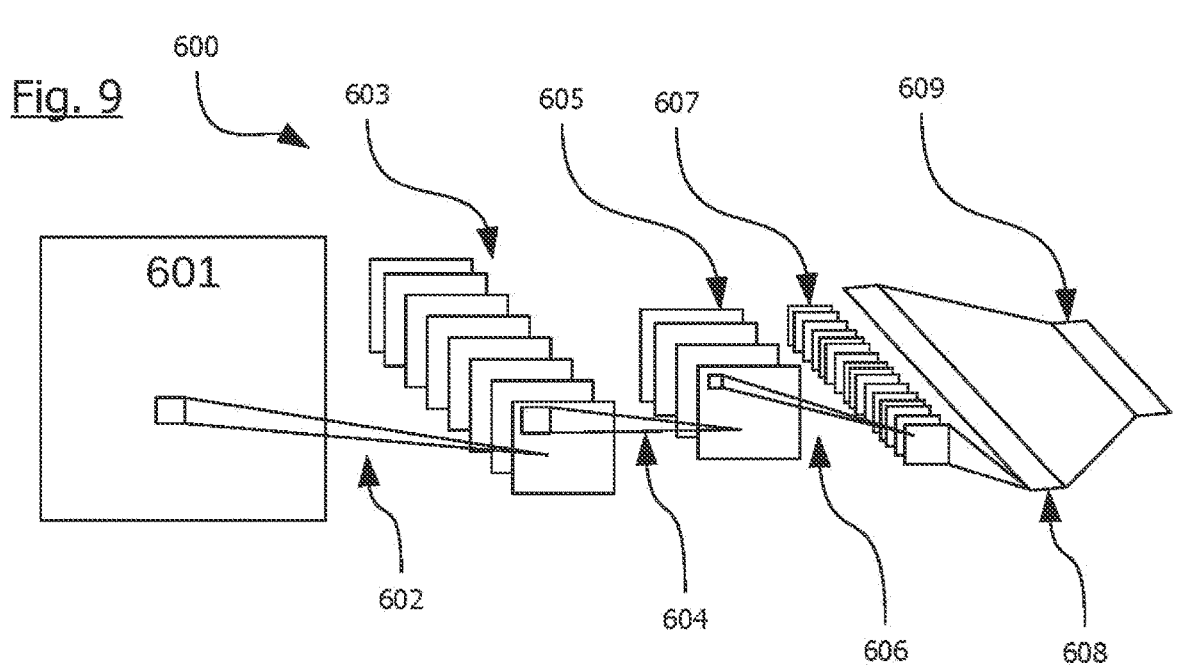
FIG. 9 illustrates a schematic of a convolutional neural network, which can be used with this invention.

FIG. 9 is a schematic of a convolutional neural network 600, which can be used to implement the inventive method and system. The schematics of FIG. 9 shows an input image tile 601, which may be processed by the neural network 600. As the neural network 600 is a convolutional neural network, a plurality of kernels are used to process the input image tile 601. In particular, each kernel scans over the pixels of the input image tile 601 in a sequential manner, for example from the top left to the bottom right in a line-by-line fashion. A parameter, the so-called stride, indicates by how many pixels each kernel is moved in every move.

Moreover, a kernel size determines the size of the patch that is scanned by the kernel. Thus, depending on the size of the input image tile 601, the kernel size and the stride, the size of the feature maps 603 in the first convolutional layer is determined. Each feature map 603 represents a feature detector. For example, a first feature map may be adapted to detect corners. Consequently, the resultant feature map 603 is a map of corners detected in the input image tile 601. A second feature map may indicate edges.

In the next layer of the convolutional neural network 600, sub sampling 604 generates four second feature maps 605. In this layer, the feature maps 603 of the previous layer are subsampled in order to generate a more compact representation of the input image tile 601. This is in particular useful to reduce the size of the convolutional neural network in order to increase training and prediction speed. From the four second feature maps 605 onward, another convolution 606 generates a greater plurality of third feature maps 607 in the same fashion as described before. From the generated third feature maps 607 the output is input of a feedforward neural network, which is fully connected and comprises two layers 608 and 609 in the described embodiment.

Importantly, the last layer 609 of the neural network 600 is a so-called soft-max layer, wherein the input image tile 601 is classified into one of many classes.

Each layer in the convolutional neural network 600 is built from a great number of neurons, i.e. activation functions, having weights. Depending on the weight and value of an input, the output of the neuron is activated or left deactivated. Possible activation functions include for example a logit, arc tan, or Gaussian functions. The training of the neural network 600 is conducted using the back propagation algorithm and using training data to determine the weights associated with the activation functions.

Many different architectures of convolutional neural networks are possible to implement the inventive aspects of the present application. For example, the number of kernels may be varied in the different convolutional layers. Also, the number of layers can be varied. Possible architectures include the VGG-net, RES-net, general adversial networks, google LeNet with inception modules.

The training of the convolutional neural network may be conducted in a cloud service such that the computation is spread across multiple machines, using parallelism to increase the training speeds.

Figure 10:
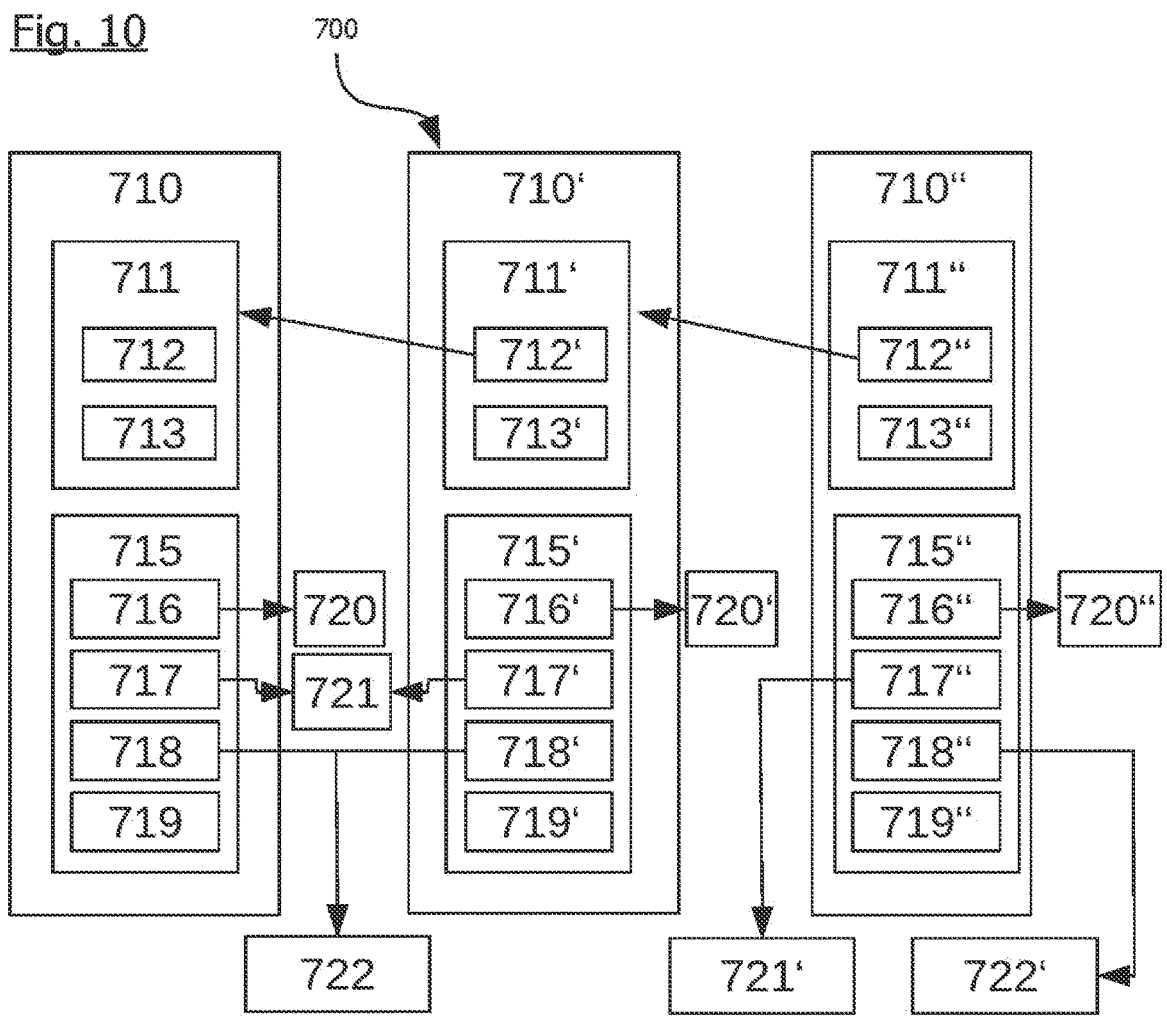
FIG. 10 illustrates a schematic of a block chain.

FIG. 10 shows a schematic of a blockchain 700, which may be used to store the information used to train the neural network 600 and/or also a trained neural network. In general, a blockchain is a continuously growing list of records, which are linked to each other. Each record represents a transaction in the blockchain. In the present case, adding data to the knowledge base by an expert E, E', E" represents a transaction and thus the fact that the data is added to the knowledge base can be recorded using the blockchain 700. In this way, it is transparent to the patient, which data was used in training the neural network 600.

FIG. 10 shows three blocks 710, 710', 710", recording at least three transactions, i.e. adding three training abnormality degree values for the image tiles. Each block can also contain more transactions but for the sake of simplicity, the following description is limited to the case of a single transaction.

For example, block 710' comprises a header 711' and a data block 715'. The header 711' comprises a hash value 712', storing the hash value of the header of the previous block 710. As a result, the block that precedes the block 710' in the blockchain 700 is uniquely identifiable. Moreover, header 711' comprises a Merkle root value 713'. The Merkle root value 713' is the hash value of the root node of a Merkle tree. The Merkle tree may be used to identify all training abnormality values used to train a neural network.

The data block 715' comprises a link to a data block 716', which is stored outside of the blockchain 700. Also, the data block 715' stores a link to an image tile 717', to which the abnormality degree value 719' is associated to. In addition, the data block 715' stores the training abnormality degree value 719' as well as a link to the whole slide image 718' of which the image tile 721 is a part of Even more, the data block 715' stores a link to the expert E, E', E" that evaluated the linked image tile of the linked whole slide image and determined the abnormality degree value stored in the block 710'.

Furthermore, the blockchain 700 can be configured to only allow experts E, E', E" to insert data into the blockchain 700, which received a proper education and which have the necessary qualifications. This can be implemented using scripting mechanisms of the blockchain technology. The scripts may define conditions that need to be fulfilled before an entry may be added to the blockchain. These mechanisms are also known as smart contracts.

It is worth pointing out that blockchain technology does not rely on a single central server but is a distributed data structure shared among all peers of a peer-to-peer network. Data is added to the blockchain using a trust mechanism, which is well-known in the art. As a result, all peers in the network usually accept the current longest chain as the most trustworthy. Moreover, the content of the blockchain 700 is publicly available and thus any user may identify all records that are stored in the blockchain 700. This allows a user/patient/doctor to review all the experts that have contributed to the blockchain 700 and their reviews of image tiles stored in the blockchain 700. This provides an unprecedented degree of transparency in the diagnostic process.

REFERENCE NUMERALS 10 method to determine abnormality value
11 whole slide image
12 Segmentation phase
13 image tiles
14 prediction phase
15 local abnormality degree value for each tile
16 evaluation phase
17 degree of abnormality
20 cancer analysis system
21 whole slide image
22 segmentation entity
23 set of image tiles
24 computation entity
25 knowledgebase
26 training data
27 result
30 image processing entity
100 prediction phase
103 pairs of abnormality and likelihood
104 list of pairs L_w
110 partitioning phase
120 abnormality prediction phase
130 List creation
200 priorization phase
201 pairs of priorities and 210 Prioritize
220 sorting phase
230 candidate elimination phase
240 distribution phase
300 decision making phase
310 review phase
320 abnormality determination phase
330 KB extension phase
400 improvement phase
410 accuracy comparison phase
420 Determination phase
430 Network replacement phase
440 Leave network
500 DCAS
501 whole slide image
502 set of image tiles
503 list of abnormality degree and likelihood pairs
504 list of candidate image tiles
505, 505', 505" validation set
506 validation training data
507 independent validation data
508 validation data
509 training data
510 analysis system
511 segmentation entity
512 computation entity
513 priorization entity
514 communication interface
515 Validation Database
516 independent validation cohort
517 knowledgebase
518 testing entity
519 degree of abnormality
600 convolutional Neural Network
601 Input image tile
602 first convolution
603 eight first feature maps
604 subsampling
605 four second feature maps
606 second convolution
607 16 third feature maps
608 feed forward layer/fully connected layer
609 output layer
700 blockchain
710, 710', 710" block
711, 711', 711" header
712, 712', 712" hash value of previous header
713, 713', 713" Merkle root
714, 714', 714" WID hash
715, 715', 715" Data block
716, 716', 716" link to data block
717, 717', 717" link to image tile
718, 718', 718" link to whole slide image
719, 719', 719" abnormality degree
720, 720', 720" data block
721, 721', 721" image tile
722 whole slide image
E, E', E" expert
w whole slide image
t_1, . . . , t_j . . . , t_n sequence of image tiles
l_j likelihood
a_j abnormality degree
p priority
L_w List of abnormal events for whole slide image
S_w List
C subset of S_w
V list of experts assignments
a_w final abnormality degree value
VB Validation database

The invention claimed is:

1. A method to determine a degree of abnormality, the method comprising the following steps:
   a) receiving a whole slide image (11, w, 722), the whole slide image (11, w, 722) depicting at least a portion of a cell, in particular a human cell;
   b) classifying at least one image tile (13, 601, 721, 721', 721") of the whole slide image (11, w, 722) using a neural network (600) to determine a local abnormality degree value (15, a_j, 519, 719, 719', 719") associated with the at least one image tile (13, 601, 721, 721', 721"), the local abnormality degree value (15, a_j, 519, 719, 719', 719") indicating a likelihood that the associated at least one image tile depicts at least a part of a cancerous cell; and
   c) determining a degree of abnormality (17) for the whole slide image (11, w, 722) based on the local abnormality degree value (15, a_j, 519, 719, 719', 719") for the at least one image tile (13, 601, 721, 721', 721"),
   wherein the neural network (600) comprises:
      at least fifty layers,
      at least twenty pooling layers,
      at least forty convolutional layers,
      at least twenty kernels in each convolutional layer, and/or
      at least one fully connected layer (608).

2. The method of claim 1, characterized in that
   the degree of abnormality (17) for the whole slide image (11, w, 722) is indicated by a function, in particular a max-function, a statistical aggregation of the local abnormality degree value (15, a_j, 519, 719, 719', 719") or an average function dependent on the local abnormality degree value (15, a_j, 519, 719, 719', 719").

3. The method of claim 1, characterized by:
   Segmenting the whole slide image (11, w, 722) into a plurality of image tiles (13, 23, 502, t_1, . . . , t_n), the size of each image tile being equal, in particular using a k-means clustering algorithm.

4. A non-transitory computer-readable medium storing instructions that, when executed by at least one processor, cause the at least one processor to implement a method according to claim 1.

5. A method to determine a degree of abnormality, the method comprising the following steps:
   a) receiving a whole slide image (11, w, 722), the whole slide image (11, w, 722) depicting at least a portion of a cell, in particular a human cell;
   b) classifying at least one image tile (13, 601, 721, 721', 721") of the whole slide image (11, w, 722) using a neural network (600) to determine a local abnormality degree value (15, a_j, 519, 719, 719', 719") associated with the at least one image tile (13, 601, 721, 721', 721"), the local abnormality degree value (15, a_j, 519, 719, 719', 719") indicating a likelihood that the associated at least one image tile depicts at least a part of a cancerous cell; and
   c) determining a degree of abnormality (17) for the whole slide image (11, w, 722) based on the local abnormality degree value (15, a_j, 519, 719, 719', 719") for the at least one image tile (13, 601, 721, 721', 721"),
   wherein the neural network (600) is trained with training data (26, 509) stored in a knowledgebase (25, 507), the training data (26, 509) including a plurality of tuples, each tuple indicating an image tile (13, 601, 721, 721', 721"), a training abnormality degree value (15, 519, 719, 719', 719", a_j) and a likelihood value (l_j), and wherein the training abnormality degree value (a_w) for at least a subset of the image tiles (C) determined by a human expert (E) is stored in a block (710, 710', 710") of a blockchain (700).

6. The method of claim 5,
characterized by
receiving an update whole slide image (11, 21, 501, 722, w) to update a knowledgebase (25, 507);
segmenting the update whole slide image (11, 21, 501, 722, w) into a plurality of image tiles (13, 601, 721, 721', 721");
determining a training abnormality degree value (a_w) for each image tile of at least one subset of the plurality of image tiles (C), in particular by a human expert (E); and
updating the knowledgebase (25, 507) with the subset of the plurality of image tiles (C) and the associated training abnormality degree values (a_w) if it is determined that adding the subset of the plurality of image tiles (C) and the associated training abnormality degree values (a_w) improves the accuracy of the neural network when trained with the updated knowledgebase (25, 507).

7. The method of claim 6,
characterized in that
updating the knowledgebase (25, 507) further comprises:
computing a predicted abnormality degree value (a_j) and an associated likelihood value (l_j) for each of the plurality of image tiles (13, 601, 721, 721', 721") using the neural network;
determining a priority value (p_j) based on the predicted abnormality degree value (a_j) and the associated likelihood value (l_j) for each of the plurality of image tiles (13, 601, 721, 721', 721"); and
determining the subset of the image tiles (C) based on the determined priority (p_j) values.

8. The method of claim 6,
characterized in that
determining that adding the subset of the image tiles (C) and the associated training abnormality degree values (a_w) improves the accuracy of the neural network when trained with the updated knowledgebase (25, 507) comprises:
updating a validation database (515) with the subset of the image tiles (C) and the associated training abnormality degree values (a_w), the validation database in particular including at least a subset of the knowledge base;
training the neural network (600) using the validation database (515);
using the neural network (600) trained on the validation database (515) to predict the data in an independent validation cohort (516) to compute a first accuracy value;
using the neural network trained (600) on the knowledgebase (25, 517) to predict the data in the independent validation cohort (516) to compute a second accuracy value; and
comparing the first and the second accuracy values to determine whether adding the subset of the image tiles (C) and the associated training abnormality degree values (a_w) improves the accuracy of the neural network (600) when trained with the updated knowledgebase (25, 507).

9. The method of claim 6,
characterized in that
each block (710, 710', 710") of the blockchain (700) comprises a header (711, 711', 711") comprising a hash value (712, 712', 712") of the header of a previous block and a hash value of a the root node of a merkle tree (713, 713', 713"), the merkle tree indicating all data stored in the knowledgebase (25, 517).

10. The method of claim 6,
characterized in that
each block (710, 710', 710") of the blockchain (700) comprises a data block (715, 715', 715") comprising a link to an associated image tile (717, 717', 717"), a link to an associated whole slide image (718, 718', 718") and a training abnormality degree value (719, 719', 719") determined by the expert (E, E', E") and associated with the respective image tile (717, 717', 717").

11. A distributed cancer analysis system (500), comprising the following components:
a segmentation entity (511) adapted to receive a whole slide image (501), the whole slide image (501) depicting at least a portion of a cell, wherein the segmentation entity (511) is further adapted to segment the whole slide image (501) into a plurality of images tiles (504);
a computation entity (512) adapted to compute a degree of abnormality (519) for the whole slide image (501) using a neural network (600), wherein the computation entity (512) is further adapted to compute the degree of abnormality (17) for the whole slide image (11, w, 722) using a function depending on local abnormality degree values (15, a_j, 519, 719, 719', 719") associated with the plurality of image tiles (13, 601, 721, 721', 721");
a communication interface (514) adapted to distribute at least a subset of the plurality of image tiles (C) to at least one expert (E); and
a prioritization entity (513) adapted to determine the subset of the plurality of image tiles (C) to be transmitted to the at least one expert (E, E', E") by the communication interface (514),
wherein the prioritization entity (513) is further adapted to determine the subset of the plurality of image tiles (C) based on a computed priority value for each image tile (502).

12. The distributed cancer analysis system (500) according to claim 11, characterized by:
a knowledgebase (517) comprising training data (509),
wherein the computation entity (512) is further adapted to train the neural network (600) using the training data (509).

13. The distributed cancer analysis system (500) according to claim 12,
characterized by,
a testing entity (518) adapted to:
receive validation training data (506) of a validation database (515), the validation training data (506) comprising at least one validation set (505, 505', 505"), the validation database (515) in particular including at least a subset of the knowledge base, determined by the at least one expert (E, E', E");
train the neural network using the received validation data (506);

use the neural network trained on the validation data to predict the data in an independent validation cohort to compute a first accuracy value;

use the neural network trained on the knowledgebase to predict the data in an independent validation cohort to compute a second accuracy value; and compare the first and the second accuracy values to determine whether updating the knowledgebase (25, 507) with the subset of the image tiles (C) and associated training abnormality degree values (a_w) improves the accuracy of the neural network when trained with the updated knowledgebase (25, 507).

14. The distributed cancer analysis system (500) of claim 11, characterized by a blockchain (700) adapted to store a training abnormality degree value (719, 719', 719") for each of the subsets of the image tiles (C) in a block (710, 710', 710"), the training abnormality degree value determined by a human expert (E, E', E").

\* \* \* \* \*